United States Patent [19]

Skaletsky

[11] Patent Number: 4,892,824

[45] Date of Patent: Jan. 9, 1990

[54] FAST TRACK METHOD FOR PRODUCING MONOCLONAL BI-SPECIFIC IMMUNOGLOBULINS

[75] Inventor: Eileen Skaletsky, San Diego, Calif.

[73] Assignee: Synbiotics Corporation, San Diego, Calif.

[21] Appl. No.: 168,378

[22] Filed: Mar. 15, 1988

[51] Int. Cl.[4] .................. C12N 15/00; C12N 5/00; C12N 33/53; C12R 1/91

[52] U.S. Cl. .................... 435/172.2; 435/240.27; 435/948; 435/70.21; 436/548; 935/89; 935/90; 935/92; 935/93; 935/102

[58] Field of Search ............ 435/240.27, 68, 172.2; 935/89, 90, 92, 93, 102; 436/548

[56] References Cited

U.S. PATENT DOCUMENTS 4,714,681 12/1987 Reading .................. 435/240.27

OTHER PUBLICATIONS

Milstein et al., Immunology Today, vol. 5, pp. 299–304.
Corvalan et al., Cancer Immunol. Immunotherap., vol. 24, pp. 127–132, 1987.
Clark et al., J.N.C.I., vol. 79, pp. 1393–1401, 1987.
Suresh et al., Methods in Enzy., vol. 121, pp. 210–228, 1986.
Galpe et al., Methods in Enzy., vol. 73, pp. 3–46, 1981.

*Primary Examiner*—Christine M. Nucker
*Assistant Examiner*—Karen I. Kruper

[57] ABSTRACT

An accelerated method for making culturable cells which express bi-specific immunoglobulin employs a three cell fusion procedure which simultaneously fuses a myeloma cell with two B lymphocytes, each of which expresses antibody having a different antigenic specificity.

13 Claims, No Drawings

FAST TRACK METHOD FOR PRODUCING MONOCLONAL BI-SPECIFIC IMMUNOGLOBULINS

BACKGROUND

The invention relates to methods for making hybridomas which produce monoclonal immunoglobulin. More particularly, the invention relates to methods for making polyomas which express monoclonal bi-specific immunoglobulin.

There are five classes of naturally occurring immunoglobulins, viz. IgA, IgD, IgE, IgG, and IgM. IgG is the most common immunoglobulin. Immunoglobulins include at least two peptide chains, viz. a heavy chain and a light chain. Each light chain is linked by disulfide bonds to a corresponding heavy chain. Bi-valent immunoglobulin includes two pairs of paired heavy and light chains. Each of the two heavy chains are linked to one another by disulfide bonds. Each class of immunoglobulin is characterized by the structure of its heavy chain. In turn, each class of immunoglobulin may be subdivided into subclasses which are characterized by more subtle distinctions within the structure of the heavy chains. And finally, immunoglobulins can be further distinguished by the structure of the light chain, viz. either lambda or kappa light chains. Either type of light chain may occur in combination with any of the classes or subclasses of heavy chains.

Each of the heavy and light chains are divided into constant regions and variable regions. The constant regions provide the over all molecular structure of each class of immunoglobulin and the site or focus of various molecular interactions with respect to regulatory factors. The variable regions of paired heavy and light chains are juxtaposed to one another to form a combined variable region. Each combined variable region defines an antigen binding site and a framework for the antigen binding site. An antigen binding site is a site on the immunoglobulin to which the antigen binds. Each antigen binding site corresponds to one valency. Bi-valent immunoglobulins include two antigen binding sites. The antigen binding sites of naturally occurring bi-valent immunoglobulin are identical to one another, i.e. naturally occurring immunoglobulins are mono-specific.

Immunoglobulins are produced by antibody expressing cells, e.g. plasma cells and various other activated B lymphocytes. Any given naturally occurring antibody expressing cell expresses only one type of mono-specific immunoglobulin. However, the vascular and lymphatic systems contain many different such antibody expressing cells. Hence, serum antibody may include many different immunoglobulins having many different specificities. Serum antibody is therefore said to be polyclonal.

In 1975, Kohler and Milstein (Nature, vol. 256, pp 495–497) developed a technique for making hybridomas. Hybridomas are hybrid cells created by fusing lymphocytes or other antibody expressing cells with myeloma cells, i.e. fusion partner cells. Myeloma cells are neoplastic plasma cells which preferably do not express antibody and which which are culturable, i.e. they may be maintained in culture indefinitely. On the other hand, lymphocytes are antibody expressing leukocytes. Lymphocytes are nonculturable, i.e. they can not be maintained in culture for an extended period. Some of the cellular fusion products of these two cell types will combine the properties of both parent cells, viz. the ability to express immunoglobulin and the ability to be maintained in culture for an extended period. The specificity of the immunoglobulin expressed by the cellular fusion product or hybridoma is determined by the specificity of the immunoglobulin expressed by the parent lymphocyte. When properly screened and cloned, the hybridomas can be grown in culture for an extended period and will produce large quantities of uniform mono-specific immunoglobulin, i.e. monoclonal immunoglobulin.

The advent of hybridoma technology caused a rapid proliferation of new developments and applications for monoclonal immunoglobulin. Included within the new developments were new methods for fabricating bi-specific immunoglobulin.

A bi-specific immunoglobulin is an immunoglobulin having two different antigenic specificities. Bi-specific immunoglobulin is sometimes known as bi-functional immunoglobulin. Bi-specific immunoglobulin is useful in various immunoassay procedures, therapies, and other uses.

The initial efforts to produce bi-specific immunoglobulin employed chemical methods on polyclonal immunoglobulin. The first step of these methods involved a reductive dissociation of each of two samples of polyclonal immnoglobulin. The two samples of polyclonal immunglobulin are chosen to have different specificities from one another. After the reductive dissociation, the two samples are then combined and allowed to undergo an oxidative re-association. In the first step, the disulfide linkages of the polyclonal immunoglobulin are broken by exposure to reducing conditions. In the second step, the dissociated subunits are then allowed to reassemble under oxidating conditions. It was found that the reassembly process is somewhat random and that the reassembly of immunoglobulin into the desired bi-specific form was somewhat inefficient.

A more efficient method for chemically producing bi-specific immunoglobulin was recently disclosed by Maureen Brennan et al. (Science, vol. 229, pp 81–83 (1985)). Brennan discloses the use of monoclonal immunoglobulin as the starting material. Two monoclonal antibodies, each having a different antigenic specificity, are employed. Unfortunately, the method of Brennan involves a limited pepsin hydrolysis of the starting antibodies and therefore produces a bi-specific F(ab')2 fragment instead of an intact immunoglobulin molecule (IgG). However, the chemistry of Brennan's process is relatively efficient.

In 1984, Christopher Reading (U.S. Pat. No. 4,474,893) disclosed a method for making triomas and quadromas which express recombinant bi-specific immunoglobulin. Reading defines a trioma to be a cellular fusion product which results from the fusion of a lymphocyte and a hybridoma cell or other such fusion partner cells which are culturable and antibody expressing. A quadroma is defined to be the cellular fusion product which results from the fusion of two hybridomas, i.e. two fusion partner cells. Quadromas are sometimes also known as hybrid-hybridomas. With respect to the trioma, Reading points out that, if the hybridoma and the lymphocyte each express different antibodies, i e. immunoglobulin having different specificities, then the resultant trioma may express a recombinant bi-specific immunoglobulin. Similarly, with respect to the quadroma, if the two hybridomas each express different antibodies, then the resultant quadroma may express a recombinant bi-specific immunoglobulin. It is assumed that, for any given trioma or quadroma, the sites of recombination will be randomly distributed within the genome.

Other workers have made hetero-hybridomas. A hetero-hybridoma is a cellular fusion product derived from the cells of two different species. The fusion may be between a myeloma from one species and a lymphocyte from a different species; between a hybridoma derived from one species and a lymphocyte from a different species; or between two hybridomas derived from different species. These hetero-hybridomas express recombinant monoclonal immunoglobulin which includes portions of each of the two species. However, such hetero-hybridomas have not been reported to produce bi-specific monoclonal immunoglobulin.

The relative efficiency of the use of triomas and quadromas for producing bi-specific immunoglobulin is compared to the chemical methods by Brennan (supra). Brennan states that, employing her method and starting with a supply of two types of monoclonal immunoglobulin, a chemist can produce pure bi-specific immunoglobulin within one week. By comparison, Brennan indicates that it would require a significantly longer period of time to produce purified bi-specific immunoglobulin if one were required to produce a trioma or quadroma ab initio. Hence, one can infer from Brennan that the speed with which bi-specific immunoglobulin can be made is an important factor for many users.

Indeed, in certain clinical situations, it may be very important to produce bi-specific monoclonal antibodies with great speed. Reading indicates that bi-specific monoclonal antibodies can be employed as reagents for the treatment of tumors. One valency of the reagent has a specificity for the tumor; the other valency of the reagent has a specificity for a drug or toxin which is to be targeted against the tumor. However, if a patient develops a tumor having an unusual or unique tumor specific antigen, it may be necessary to make a new bi-specific monoclonal immunoglobulin to correspond to such tumor specific antigen. If a reagent employing a bi-specific monoclonal immunoglobulin is to have clinical utility, the patient's physician must have quick access to the reagent. If the reagent is custom made for the patient, it should be capable of being produced quickly.

Brennan points out that chemical method for making bi-specific immunoglobulin can be quicker than cellular methods. However, Brennan's method is premised on the pre-existance of a supply of the appropriate monoclonal immunoglobulin. If a bi-functional monoclonal immunoglobulin needs to be custom taylored to the antigenic specificity of a patient's tumor, the difference in the speed between Brennan's method and Reading's method is greatly reduced.

What is needed is a fast track method for producing bi-specific monoclonal immunoglobulin. Unlike prior art chemical methods, the fast track method should be adaptable to the production of bi-specific monoclonal immunoglobulin with new antigenic specificities. What is needed is a fast track method for producing bi-specific monoclonal immunoglobulin which by-passes the serial fusions and clonings which are employed in prior art cellular methods for making triomas and quadromas.

SUMMARY OF THE INVENTION

The invention is a fast track method for making polyomas which expresses bi-specific monoclonal immunoglobulin. The term polyoma is employed herein to designate a cellular fusion product which includes two antibody expressing cells and a myeloma cell. Polyomas are similar to the triomas and quadromas described by Reading except for their mode of production. The method for producing polyomas described herein is considerably shorter than the method for producing triomas or quadromas described by Reading because the steps for making intermediate hybridomas are eliminated. The shortening of the time required to make such polyomas can have significant clinical and commercial benefits.

Employing the fusion conditions and cellular components described herein results in the simultaneous or substantially simultaneous fusion of three cellular components into one cellular fusion product. The fusion of all three cells occurs in one short fusion step. The fusion methods employed in the prior art resulted in the fusion of two cellular components only. The prior art taught that, in order to achieve fusion of three cellular components, serial fusion steps must be performed.

After the fusion step of the fast track method, the cellular fusion products are screened to detect the formation of polyomas which express bi-specific immunoglobulin. If donor animals are appropriately inoculated and screened according to the fast track method and, if fusion conditions are employed as prescribed by the fast track method, then there will be a significant frequency of simultaneous or substantially simultaneous three cell fusion events resulting in the formation of useful polyomas. This result was unanticipated by the prior art. It is a surprising result that a fast track method can be constructed for making polyomas; it is a surprising result that the fast track method typically yields multiple successful polyomas.

An important element of the fast track method is the inoculation and screening of donor animals. In the preferred mode, two groups of animal donors are serially inoculated to produce high antibody titers. The first group of animal donors are inoculated and may be given one or more booster injections with the first antigen; similarly, the second group of animal donors are inoculated and may be given one or more booster injections with the second antigen. After the inoculations, blood samples may be drawn from the donor animals in order to monitor the antibody titer level with respect to the inoculant. Only animals with high antibody titers, i.e. good responders, are employed in subsequent steps.

In an alternative mode, only one group of donor animals is employed and each animal within the group is simultaneously or serially inoculated and boosted with both of the antigens. Unfortunately, it has been found that the frequency of animals which are high responders with respect to both antigens is relatively low. Hence, the use of a single group of animals for inoculating with both antigens is not a preferred mode of the fast track method.

The high responder animals are the animals most likely to yield a high level of antibody expressing cells. A preferred organ for providing antibody expressing cells is the spleen. In the preferred mode, the spleen is removed from the highest responder donor animal and agitated until a single cell suspension is formed. The cell count of lymphoidal splenocytes within this suspension is then determined.

The antibody expressing cells from each of the highest responder of the two groups of donor animals are then simultaneously or substantially simultaneously fused with myeloma cells or with similar transformed cells with which hybridomas can be made. This fusion step substantially differs from prior art fusion steps for hybridomas, triomas, etc. because it is a three cell fusion event. Prior art fusion steps involved only two cells, viz. one antibody expressing cell and one myeloma cell. Also, the optimal conditions for the fusion step of the fast track method are materially different from the optimal conditions for prior art fusion steps.

The prior art for making hybridomas teaches that, during the fusion step, the ratio of lyphoctes to myeloma cells should be optimized to yield the maximum yield of cellular fusion products which include only two cells, viz. one antibody expressing cell and one myeloma cell. Furthermore, the prior art for making triomas and quadromas (hybrid-hybridomas) teaches that these cellular fusion products should be made by serial fusions, each of which involve the fusion of only two cells. The ratio of cell employed in each two cell fusion event is designed to maxixize the yield of cellular fusion products involving only two cells. In contrast, the present specification teaches that, when making a polyoma by the fast track method, the ratio of three cellular entities must be considered and their relative ratioes must be adjusted so as to maximize the number of cellular fusion products which include three cells, viz. two lymphocytes (each expressing antibody having a different specificity) and one myeloma cell. The optimal ratio of lyphocytes to myeloma cells employed by the fast track method for making polyomas is substantially greater than the comparable optimal ratio of lyphocytes to myeloma cells for producing hybridomas and the like.

The fusion step is performed when myeloma cells are in their "S" phase of growth. During and after the fusion event, significant random recombination of the immunoglobulin genes will occur. The resultant bispecific immunoglobulin which is eventually expressed by polyoma will be the product of this random recombination. In essence, the precise structure of the immunoglobulin will be rendered unpredictable by this recombination.

After the fusion step, aliquots of the cellular fusion products are pipetted into the wells of microtiter plates, incubated, and screened In the preferred mode, two screening steps are followed. The first screening step merely identifies cellular fusion products which express immunoglobulin having a specificity for either of the two antigens employed during the inoculation step. Wells which test positive are then further expanded. The expanded wells are then further screened to identify monoclonal antibody which has two or more specificities, i.e. specificities for each of the antigens employed during the inoculation step.

In an alternative mode, the screening steps can be condensed. Simultaneous multiple specificities can be screened during the first screen step. However, this alternative mode entails considerably more work and may not materially hasten the production of monoclonal antibody, since the second expansion step is necessary.

In a further alternative mode, the cellular fusion products may be screened by an ELISA in which a solid phase is made of the first antigen and the enzyme labeled soluble phase is conjugated to the second antigen.

After a cellular fusion product is tentatively identified to be a polyoma which produces bispecific immunoglobulin, such polyoma is then cloned by limiting dilution. The bi-specificity of the immunoglobulin expressed by a cloned polyoma can then be further verified by passing the immunoglobulin over an affinity matrix which binds the one specificity of the immunoglobulin, then releasing the immunoglobulin from the matrix and performing an ELISA on the eluant to test for the second specificity.

DETAILED DESCRIPTION

The fast track method for making polyomas can best be illustrated by means of an example. It is the objective of the example disclosed herein to obtain a polyoma which expresses bi-specific immunoglobulin having a binding specificity for both porcine somatotropin (pST) and for feline leukemia virus envelope protein (p27)

The first antigen, i.e. porcine somatotropin (pST), is a natural growth hormone and may be isolated and purified by the method of Dellacha, J.M. and Sonenberg, M. (Journal of Biological Chemistry, vol. 239: 1515–1520 (1964), "Purification of Bovine Growth Hormone"). After purification, the pST may be conjugated to keyhole limpet hemocyanin (KLH) by standard techniques so as to enhance its immunogenicity.

The second antigen, i.e. feline leukemia virus envelope protein (p27) is the major core protein of feline leukemia virus FeLV) and has a molecular weight of 27,000. Lutz et al. first described p27 in a treatise entitled Feline Leukemia Virus (Elsevier/Amsterdam, 1980). The p27 may be obtained from FL-74 cells, a feline lymphoblastoid cell line available from the American Type Tissue Collection (Bethesda, Maryland). FL-74 cells are persistently infected with FeLV and secrete viral proteins, including p27. Purified p27 is obtained by passing FL-74 culture fluid over an affinity column to which p27-specific antibody is attached. The p27specific monoclonal antibody is commercially available from Synbiotics, Corp. (San Diego, Calif.) or may be made by methods disclosed by Lutz.

Each of the two purified antigens may then be used to inoculate donor animals. Two groups of ten Balb/c mice may be employed as the donor animals, i.e. one group for each antigen. In a preferred mode, the initial inoculation and subsequent booster injections may be made intraperitoneally. However, a final booster injection may be administered intravenously. During the inoculation period, blood samples should be regularly drawn from the donor mice in order to monitor their immune response by means of their antibody titer levels. Only the best responder from each group of mice is chosen for donating its antibody expressing cells for use in the fusion, described below. An example of a schedule and protocol of the inoculations and booster injections designed to maximize the immune response is provided as follows:

pST-KLH Inoculation Schedule

Day 1: Primary inoculation with 50 micrograms of pST-KLH in Complete Freund's adjuvent;
Day 22: First booster injection with 50 micrograms of pST-KLH in Incomplete Freund's adjuvent;
Day 29: Bleed;
Day 54: "Pre-fusion" intravenous booster injection with 25 micrograms of pST-KLH in phosphate-buffered saline;
Day 57: One mouse of the ten selected for Fusion Step.

p27 Inoculation Schedule

Day 1: Primary inoculation with 20 micrograms of p27 in Complete Freund's adjuvant;
Day 22: First booster injection with 20 micrograms of p27 in Incomplete Freund's adjuvant;
Day 29: Bleed;
Day 54: "Prefusion" intravenous booster injection with 20 micrograms of p27 in phosphate-buffered saline;
Day 57: One mouse of the ten selected for Fusion Step.

The immune response of each donor mouse is followed during the inoculation protocol in order to determine which mouse is the best responder. The immune response is monitored by measuring the antibody titer of the blood samples taken one week after each injection and on the day on which the best responder is sacrificed for use in the fusion step. Antibody titers are measured by means of ELISA's constructed with the two antigens, i.e. p27 and pST. The ELISA's are described below. A mouse is considered to be a good responder if its antibody titer is in excess of 12,000.

The best responder from each group is identified and its spleen removed. Each spleen is then placed into buffer solution and converted into a suspension of single cells by means of agitation. Cell counts of lymphoid cells in the suspensions are taken. The suspension of spleen cells are subsequently employed in a fusion step with myeloma cells.

The myeloma cells should be selectable, i.e. the growth of the myeloma cells in culture should be dependent upon a factor supplied by the culture medium. However, upon fusion with an antibody expressing cell, the resultant cellular fusion product loses its dependence upon this factor. Hence, the cellular fusion product can grow in culture in the absence of this factor. Preferred myeloma cell lines include P3X63-Agul and P3X63-Ag8.853, each of which can be supplied by American Type Tissue Collection. Directly prior to the fusion step, the myeloma cell line is placed into its "S" growth phase.

During the fusion step a cell mixture is made by combining a sample of the myeloma cells with both a sample of the suspension of spleen lymphoid cells from the best responder mouse with respect to p27 and a sample of the suspension of spleen lymphoid cells from the best responder mouse with respect to pST. Best results were found using a cell mixture having a cellular composition of 1:2:2, i.e. one part myeloma cells: two parts spleen lymphoid cells from the p27 reactive mouse: two part spleen lymphoid cells from the pST reactive mouse.

In order to induce fusion, the above cell mixture may then be combined with polyethylene glycol (PEG 1000) under standard conditions to form a 50% solution in culture medium. After one or two minutes, the resultant cell mixture is diluted with medium, i.e. Dulbecco's minimal essential medium (DMEM), 10% fetal bovine serum, hypoxanthine, aminopterin, and thymidine. The dilution is calculated to yield a cell mixture with approximately 1-1.5 x10(6)cells per milliliter. Aliquots of 0.2 milliliters of the diluted cell mixture are then pipetted into microtiter plates, preferably 96 well plates. The wells of the microtiter plates should also include a feeder layer of mouse thymocytes. The resultant fusion products are then incubated in the microtiter plates for 10-12 days.

After 10-12 days of incubation, the cellular fusion products in each microtiter well is screened for the presence of anti-p27 and/or anti-pST immunoglobulin.

In the preferred mode, a preliminary ELISA is devised for detecting immunoglobulin having specificity for either or both p27 and pST. Hence, this preliminary ELISA detects both bi-specific and mono-specific immunoglobulin. The preliminary ELISA employs microtiter plates having wells which are surface coated with both p27 and pST antigens. The preliminary ELISA also employs enzyme conjugated polyclonal antibody to mouse immunoglobulin which can catalyze a color reaction in the presence of substrate. Once these materials have been prepared, the ELISA is performed by transferring small aliquots of the supernatants from the incubating cellular fusion products to corresponding preliminary ELISA wells. After incubating in the preliminary ELISA wells, the supernatants are washed from the wells to remove unbound immunoglobulin. Labeled anti-mouse antibody is then pipetted into the preliminary ELISA wells and allowed to incubate. After the incubation, the unbound portion of the enzyme conjugate of anti-mouse antibody is washed from the wells. Substrate is then added to the wells and the bound enzyme conjugate is allowed to drive a color reaction. The development of color within a well indicates the presence of bi-specific or monospecific immunoglobulin having a specificity for either or both p27 and pST antigens. In turn, the presence of such immunoglobulin indicates the presence of a hybridoma or polyoma within the incubation well from which the supernatant was drawn.

In one example, 111 out of 1100 wells, or approximately 10% of the wells, tested positive in the above preliminary ELISA. Wells which test positive contain either hybridomas which produce mono-specific immunoglobulin having a specificity for p27 or pST or polyomas which produce bi-specific immunoglobulin. Wells which test positive may then be transferred to a second microtiter plate having 24 wells and expanded ten fold by the addition of 2 milliliters of fresh medium. The expanded cellular fusion products may then be allowed to incubate for 3-5 days.

After expanding and incubating the cellular fusion products which test positive with respect to the preliminary ELISA, the expanded cellular fusion products may then be subjected to a secondary set of two ELISA's. One of the secondary ELISA's may detect anti-p27 immunoglobulin and the other secondary ELISA may detect anti-pST immunoglobulin. The secondary ELISA's are similar to the preliminary ELISA except that, for the secondary ELISA's, two sets of microtiter plates are used, the wells of each set of plates being coated with a separate antigen, i.e. with p27 or with pST. In one example, 3 out of 111 wells of the expanded cellular fusion products, or approximately 3%, tested positive with respect to the secondary ELISA.

In an alternative primary or secondary ELISA, microtiter plates coated with a first antigen and the soluble enzyme conjugate is conjugated to a second antigen. The first antigen, which is coated onto the microtiter plates, is different from the second antigen, which is conjugated to the enzyme. For example, the microtiter plates may be coated with p27 and the enzyme label may be conjugated to pST. This alternative ELISA may also include the reverse configuration, separately or in conjunction with the first configuration. The use of these alternative ELISA's has the effect of reducing the number of false positives, i.e. positives which do not identify bi-specific immunoglobulin.

In order to reduce the possibility that some of the wells testing positive may contain more than one hybridoma or polyoma, the cellular fusion products of these wells may be cloned by limiting dilution. The cellular fusion products are diluted in media and plated into microtiter plates so that 1–5 cells are plated into each well. After a period of incubation and growth, the wells are again screened by an ELISA. Between 5 and 50% of the wells should test positive. Optionally, a second cloning by limiting dilution may also be performed. In one example, approximately 90% of the clones were found to express bi-specific immunoglobulin by this method.

The best three cloned polyomas may then be taken and injected intraperitoneally into mice to produce ascites fluid. Bi-specific monoclonal immunoglobulin can then be obtained from the ascities fluid by standard purification methods.

As a final check, the bi-specificity of the immunoglobulin may be verified by affinity chromatography. For example, pST antigen may be covalently attached to an affinity matrix. A solution which is thought to contain bi-specific immunoglobulin is then passed over the matrix material. The bi-specific immunoglobulin and/or anti-pST mono-specific immunoglobulin will bind to the matrix. Meanwhile, non-binding immunoglobulins will be eluted from the matrix. The bound immunoglobulins may then be eluted from the matrix by the addition of a releasing agent. The eluted immunoglobulins are then assayed by means of an ELISA of the type described above for detecting anti-p27 immunoglobulin. Bi-specific immunoglobulin will test positive with the ELISA and mono-specific immunoglobulin will test negative. An affinity chromatography kit which may be adapted for this assay is available from New Brunswick Scientific (Edison, N.J.) under the trade name of Pro-Disc. The kit includes a polyvinyl chloride (PVC) matrix which is cross-linked to gluteraldehyde within a polycarbonate housing. Upon contacting the matrix material with antigen, the antigen is adsorbed via the gluteraldehyde residues. The matrix material is then ready to reversibly bind the corresponding antibody.

What is claimed is:

1. A fast track method for producing one or more polyomas which express a desired bi-specific immunoglobulin having specificities for a first known hapten or antigen and a second known hapten or antigen, the first hapten or antigen being different from the second hapten or antigen, the method comprising the following steps:
   Step A: obtaining a first sample of antibody expressing cells which express a first immunoglobulin having a specificity for the first hapten or antigen; Step B: obtaining a second sample of antibody expressing cells which express a second immunoglobulin having a specificity for the second hapten or antigen; Step C: obtaining a sample of myeloma cells which are selectable and which are fusible with the antibody expressing cells of the first and second samples; then Step D: combining the sample of myeloma cells with the first and second samples of antibody expressing cells so as to form a cell mixture; then Step E: forming cellular fusion products by the addition of a fusing agent to the cell mixture, the cellular fusion products including one or more polyomas created by substantially simultaneously fusing one myeloma cell, one antibody expressing cell from the first sample, and one antibody expressing cell from the second sample; and then Step F: selecting, from among the cellular fusion products, one or more polyomas which express the bispecific immunoglobulin.

2. A fast track method for producing one or more polyomas which express a bi-specific immunoglobulin as described in claim 1, wherein:
   in said Step A, obtaining the first sample of antibody expressing cells from a first animal which has been inoculated with the first hapten or antigen and which has responded with high titers of the first immunoglobulin; and
   in said Step B, obtaining the second sample of antibody expressing cells from a second animal which has been inoculated with the second hapten or antigen and which has responded with high titers of the second immunoglobulin.

3. A fast track method for producing one or more polyomas which express a bi-specific immunoglobulin as described in claim 1, wherein:
   in said Steps A and B, obtaining the first and second samples of antibody expressing cells from an animal which has been inoculated with both the first and second haptens or antigens and which has responded with high titers of both the first and second immunoglobulins.

4. A fast track method for producing one or more polyomas which express a bi-specific immunoglobulin as described in claim 1, wherein:
   in said Step D, the cell mixture having a cellular composition with more cells from each of the first and second samples of antibody expressing cells than from the sample of myeloma cells.

5. A fast track method for producing one or more polyomas which express a bi-specific immunoglobulin as described in claim 1, wherein:
   in said Step A, the antibody expressing cells of the first sample are lymphocytes taken from the spleen of a a first animal which has a high antibody titer with respect to the first antigen,
   in said Step B, the antibody expressing cells of the second sample are lymphocytes taken from the spleen of a a second animal which has a high antibody titer with respect to the second antigen,
   in said Step D, the cell mixture having a cellular composition with a ratio of substantially 2:2:1 (lymphocytes of the first sample: lymphocytes of the second sample: myeloma cells).

6. A fast track method for producing one or more polyomas which express a bi-specific immunoglobulin as described in claim 1, wherein:
   in said Step F, selecting one or more polyomas according to the following Substeps:
   Substep F.1: preliminarily screening the cellular fusion product of said Step E for identifying polyomas which express immunoglobulin having specificity for either or both the first hapten or antigen and the second hapten or antigen; and then
   Substep F.2: secondarily screening the polyomas identified in the preliminary screening of said Substep F.1 for identifying polyomas which express the bi-specific immunoglobulin having specificities for both the first hapten or antigen and the second hapten or antigen.

7. A fast track method for producing one or more polyomas which express a bi-specific immunoglobulin as described in claim 1, wherein:
in said Step F, selecting one or more polyomas according to the following Substeps:
Substep F.1: diluting the cellular fusion products with a medium which promotes the preferential growth of polyomas and plating aliquots of the cellular fusion products into microtiter plates for isolating individual polyomas; then
Substep F.2: incubating the aliquots of cellular fusion products within the microtiter plate; then
Substep F.3: assaying the medium from each of the aliquots which were incubated in said Substep F.2 for detecting positive aliquots which express an immunoglobulin having specificity for the first hapten or antigen and/or the second hapten or antigen; then
Substep F.4: expanding the positive aliquots detected in said Substep F.3 by adding more of the medium; then
Substep F.5: incubating each of the positive aliquots which were expanded in said Substep F.4; then
Substep F.6: assaying the media from each of the positive aliquots which were incubated in said Substep F.5 for detecting doubly positive aliquots which express bi-specific immunoglobulin having specificities for both the first hapten or antigen and the second hapten or antigen; and then
Substep F.7: selecting one or more of the doubly positive aliquots detected in said Substep F.6 and isolating one or more polyomas therefrom.

8. A fast track method for producing one or more polyomas which express a bi-specific immunoglobulin having specificities for a first hapten or antigen and a second hapten or antigen, the first hapten or antigen being different from the second hapten or antigen, the method comprising the following steps:
Step A: obtaining a first sample of antibody expressing cells from a first animal which has been inoculated with the first hapten or antigen and which has responded with high titers of a first immunoglobulin having specificity for the first hapten or antigen;
Step B: obtaining a second sample of antibody expressing cells from a second animal which has been inoculated with the second hapten or antigen and which has responded with high titers of a second immunoglobulin having a specificity for the second hapten or antigen;
Step C: obtaining a sample of myeloma cells which are selectable and which are fusable with the antibody expressing cells of the first and second samples; then
Step D: combining the sample of myeloma cells with the first and second samples of antibody expressing cells so as to form a cell mixture having a cellular composition with more cells from each of the first and second samples of antibody expressing cells than from the sample of myeloma cells; then
Step E: forming cellular fusion products by the addition of a fusing agent to the cell mixture, the cellular fusion products including one or more polyomas created by substantially simultaneously fusing one myeloma cell, one antibody expressing cell from the first sample, and one antibody expressing cell from the second sample; and then Step F: selecting, from among the cellular fusion products, one or more polyomas which express the bi-specific immunoglobulin.

9. A fast track method for producing one or more polyomas which express a bi-specific immunoglobulin as described in claim 8, wherein:
in said Step F, selecting one or more polyomas according to the following Substeps:
Substep F.1: diluting the cellular fusion products with a medium which promotes the preferential growth of polyomas and plating aliquots of the cellular fusion products into microtiter plates for isolating individual polyomas; then
Substep F.2: incubating the aliquots of cellular fusion products within the microtiter plate; then
Substep F.3: assaying the medium from each of the aliquots which were incubated in said Substep F.2 for detecting positive aliquots which express an immunoglobulin having specificity for the first hapten or antigen and/or the second hapten or antigen; then
Substep F.4: expanding the positive aliquots detected in said Substep F.3 by adding more of the medium; then
Substep F.5: incubating each of the positive aliquots which were expanded in said Substep F.4; then
Substep F.6: assaying the media from each of the positive aliquots which were incubated in said Substep F.5 for detecting douly positive aliquots which express bi-specific immunoglobulin having specificities for both the first hapten or antigen and the second hapten or antigen; and then
Substep F.7: selecting one or more of the doubly positive aliquots detected in said Substep F.6 and isolating one or more polyomas therefrom.

10. A fast track method for producing one or more polyomas which express a bi-specific immunoglobulin as described in claim 9, wherein:
in said Step A, the antibody expressing cells of the first sample are lymphocytes taken from the spleen of a a first animal which has a high antibody titer with respect to the first antigen,
in said Step B, the antibody expressing cells of the second sample are lymphocytes taken from the spleen of a a second animal which has a high antibody titer with respect to the second antigen,
in said Step D, the cell mixture having a cellular composition with a ratio of substantially 2:2:1 (lymphocytes of the first sample: lymphocytes of the second sample: myeloma cells).

11. A fast track method for producing one or more polyomas which express a bi-specific immunoglobulin having specificities for a first hapten or antigen and a second hapten or antigen, the first hapten or antigen being different from the second hapten or antigen, the method comprising the following steps:
Step A: obtaining a first sample of antibody expressing cells from a first animal which has been inoculated with the first hapten or antigen and which has responded with high titers of a first immunoglobulin having specificity for the first hapten or antigen;
Step B: obtaining a second sample of antibody expressing cells from a second animal which has been inoculated with the second hapten or antigen and which has responded with high titers of a second immunoglobulin having a specificity for the second hapten or antigen;

Step C: obtaining a sample of myeloma cells which are selectable and which are fusable with the antibody expressing cells of the first and second samples; then Step D: combining the sample of myeloma cells with the first and second samples of antibody expressing cells so as to form a cell mixture having a cellular composition with more cells from each of the first and second samples of antibody expressing cells than from the sample of myeloma cells; then Step E: forming cellular fusion products by the addition of a fusing agent to the cell mixture, the cellular fusion products including one or more polyomas created by substantially simultaneously fusing three cells, viz. one myeloma cell, one antibody expressing cell from the first sample, and one antibody expressing cell from the second sample; and then Step F: selecting, from among the cellular fusion products, one or more polyomas which express the bi-specific immunoglobulin by means of;

Substep F.1: preliminarily screening the cellular fusion product of said Step E for identifying polyomas which express immunoglobulin having specificity for either or both the first hapten or antigen and the second hapten or antigen; and then Substep F.2: secondarily screening the polyomas identified in the preliminary screening of said Substep F.1 for identifying polyomas which express the bi-specific immunoglobulin having specificity for both the first hapten or antigen and the second hapten or antigen.

12. A fast track method for producing a desired bispecific immunoglobulin having specificity for both a first known hapten or antigen and a second known hapten or antigen, the first hapten or antigen being different from the second hapten or antigen, the method comprising the following steps:

Step A: producing a polyoma, which expresses a bispecific immunoglobulin, by means of a substantially simultaneous fusion of one myeloma, one first antibody expressing cell, and one second antibody expressing cell, the first antibody expressing cell expressing an immunoglobulin having specificity for the first hapten or antigen and the second antibody expressing cell expressing an immunoglobulin having specificity for the second hapten or antigen, the resultant polyoma being of the type which expresses a bispecific immunoglobulin; then Step B: culturing the polyoma produced in said Step A for expressing the bispecific immunoglobulin; and then Step C: collecting and purifying the bispecific immunoglobulin which is expressed by the polyoma cultured in said Step B.

13. In an improved method for producing culturable cells which express a bi-specific immunoglobulin, the method being of the type which employs the following old steps:

Step A: obtaining a first sample of antibody expressing cells which are non-immortalized and which express a first immunoglobulin having a first specificity; then Step B: forming cellular fusion products by the addition of a fusing agent to a cell mixture, the cell mixture including fusion partner cells and the antibody expressing cells from the first sample, the fusion partner cells being culturable and fusable with the antibody expressing cells from the first sample, the cellular fusion products including culturable cells which express the bi-specific immunoglobulin, and then Step C: selecting, from among the cellular fusion products, one or more culturable cells which express the bi-specific immunoglobulin, wherein the improvement comprises the following additional steps:

Step A.1: prior to said Step B, obtaining a second sample of antibody expressing cells which are non-immortalized and which express a second immunoglobulin having a second specificity, the second specificity being different from the first specificity; and in said Step B, the cell mixture including fusion partner cells and antibody expressing cells from both the first and second samples, the fusion partner cells being substantially simultaneously fusable with the antibody expressing cells from both the first and second samples.

* * * * *